United States Patent [19]

Takano

[11] Patent Number: 4,835,170
[45] Date of Patent: May 30, 1989

[54] SEED DISINFECTANT COMPOSITION

[75] Inventor: Hirotaka Takano, Nishinomiya, Japan

[73] Assignee: Sumitomo Chemical Company, Limited, Osaka, Japan

[21] Appl. No.: 95,822

[22] Filed: Sep. 10, 1987

[30] Foreign Application Priority Data

Sep. 25, 1986 [JP] Japan ................................ 61-227624

[51] Int. Cl.$^4$ ...................... A01N 43/64; A01N 37/52
[52] U.S. Cl. ..................................... 514/383; 514/634
[58] Field of Search .................... 71/76; 514/383, 635, 514/634, 636

[56] References Cited

U.S. PATENT DOCUMENTS 3,890,446  6/1975  Brown et al. ........................ 514/634
4,435,203  3/1984  Funaki et al. ....................... 514/383
4,554,007  11/1985 Funaki et al. ........................... 71/76

FOREIGN PATENT DOCUMENTS 61-63606  4/1986  Japan .

OTHER PUBLICATIONS

Translation of JP Patent No.: JP-A-61/63606, Takand et al., 4/1/86.
C. R. Worthing: "The Pesticide Manual", 7th edition, 1983, The British Crop Protection Council, Groydon, GB; p. 305, paragraph 3.

Primary Examiner—Allen J. Robinson
Assistant Examiner—Raymond J. Henley, III
Attorney, Agent, or Firm—Stevens, Davis, Miller & Mosher

[57] ABSTRACT

A seed disinfectant composition comprising effective amounts of:
(A) (E)-1-(2,4-dichlorophenyl)-4,4-dimethyl-2-(1,2,4-triazol-1-yl)-1-penten-3-ol containing not less than 50% by weight of (-)-(E)-1-(2,4-dichlorophenyl)-4,4-dimethyl-2-(1,2,4-triazol-1-yl)-1-penten-3 -ol and
(B) a salt of 1,1'-iminodi(octamethylene)diguanidine as active ingredients, the weight ratio of (A)/(B) ranging from 1/1 to 1/1,000, and optionally an inert carrier. The seed disinfectant composition is effective on preventing seed born diseases.

1 Claim, No Drawings

SEED DISINFECTANT COMPOSITION

The present invention relates to a seed disinfectant composition comprising an inert carrier and (E)-1-(2,4-dichlorophenyl)-4,4-dimethyl-2-(1,2,4-triazol-1-yl)-1-penten-3-ol containing not less than 50% by weight of (-)-(E)-1-(2,4-dichlorophenyl)-4, 4-dimethyl-2-(1,2,4-triazol-1-yl)-1-penten-3-ol and a salt of 1,1'-iminodi-(cotamethylene)diguanidine as active ingredients.

Heretofore, benomyl thiophanate-methyl, thiram, carboxin, PCNB, organic mercury and admixtures thereof have been used to prevent seed borne diseases.

However, the commercially available disinfectants mentioned above have effects only on limited diseases, and such a problem arises that these disinfectants lose their effects of preventing seed born diseases on resistant fungi which have appeared among the disease on which these disinfectants had antifungal effects before.

In view of this situation, the present inventor have made extensive research to develop a seed disinfectant having a wide antifungal spectrum and showing a stable effect of preventing diseases on the abovementioned resistant fungi. As a result, it has been found that a seed disinfectant composition comprising (E)-1-(2,4-dichlorophenyl)-4,4-dimethyl-2-(1, 2,4-triazol-1-yl)-1-penten-3-ol containing not less than 50% by weight of (-)-(E)-1-(2,4-dichlorophenyl)-4,4-dimethyl -2-(1,2,4-triazol-1-yl)-1-penten-3-ol (hereinafter referred to as Compound A) and a salt of 1,1'-iminodi (octamethylene)diguanidine (hereinafter referred to as Compound B) as active ingredients has not only all the properties mentioned above but also an excellent synergistic effect and germination-accelerating effect.

Thus, according to the present invention, there is provided a seed disinfectant composition comprising effective amounts of (A) (E)-1-(2,4-dichlorophenyl)-4,4-dimethyl-2-(1, 2,4-triazol-1-yl)-1-penten-3-ol containing not less than 50% by weight of (-)-(E)-1-(2,4-dichlorophenyl)-4, 4-dimethyl-2-(1,2,4-triazol-1-yl)-1penten-3-ol and (B) a salt of 1,1'-iminodi(octamethylene)diguanidine as active ingredients, the weight ratio of (A)/(B) ranging from 1/1 to 1/1,000.

Compound A, one of the active ingredients of the seed disinfectant composition of the present invention, is a compound selected from the group consisting of the compounds disclosed in Japanese Patent Application Kokai (Laid-Open) Nos. 124,771/80 and 99,575/82. In other words, Compound A may be a racemic compound, a racemic mixture containing more than 50% by weight of (-)-(E)-1-(2,4-dichlorophenyl)-4,4-dimethyl-2-(1, 2,4-triazol-1-yl)-1-penten-3-ol and a pure (-)-(E)-1-(2,4-dichlorophenyl)-4,4-dimethyl-2-(1, 2,4-triazol-1-yl)-1-penten-3-ol. Compound B is known as a fungicide to various diseases of fruits, vegetables, wheat and the like. The salts of Compound B are organic salts such as acetate and the like and inorganic salts such as chloride, nitrate, sulfate and the like.

From the viewpoint of exertion of disinfectant properties, it is necessary that Compound A contains not less than 50% by weight of (-)-(E)-1-(2,4-dichlorophenyl)-4,4-dimethyl-2-(1, 2,4-triazol-1-yl)-1-penten-3-ol (hereinafter referred to as (-)-enantiomer), and since the more Compound A contains (-)-enantiomer, the greater the disinfectant effect becomes, it is preferable that Compound A contains not less than 80% by weight of (-)-enantiomer, more preferably, it is substantially pure (-)-enantiomer (purity: 90% by weight or more).

The seed disinfectant composition of the present invention can be used as it is, though it is usually used in admixture with an inert carrier. If necessary, various adjuvants for formulation are added such as surface active agents, wetting agents, sticking agents, thickeners, stabilizers and the like depending upon the use, to formulate the seed disinfectant to a preparation such as a wettable powder, a dust, a flowable concentrate, an emulsifiable concentrate or the like. There can be also used a mixture of both preparations of Compound A and Compound B. The total content of the active ingredients in the preparations is preferably from 0.1 to 99.9% by weight, more preferably 0.1 to 80% by weight. The weight ratio of Compound A to a salt of Compound B is from 1/1 to 1/1,000, preferably 1/1 to 1/100.

The carriers in the above preparation include solid carriers such as a fine powder, a granule and the like of kaoline clay, attapulgite clay, bentonite, acid clay, pyrophylite, talc, diatomaceous earth, calcite, walnut shell powder, urea, ammonium sulfate, synthetic hydrous silica and the like and liquid carriers such as, for example, xylene, methylnaphthalene and the like; alcohols, for example, isopropanol, ethylene glycol, Cellosolve and the like; ketones, for example, acetone, cyclohexanone, isophorone and the like; vegetable oils such as soy oil, cottonseed oil and the like; dimethyl sulfoxide; acetonitrile; water; etc. Surface active agents used for emulsifying, dispersing, wetting-spreading and the like include anionic surface active agents such as alkylsulfuric esters, alkyl sulfonates, aryl sulfonates, dialkyl sulfosuccinates, polyoxyethylene alkyl aryl ether phosphoric esters, naphthalene sulfonic acid-formaldehyde condensates and the like and nonionic surface active agents such as polyoxyethylene alkyl ethers, polyoxyethylene alkylaryl ethers, polyoxyethylene-polyoxypropylene block copolymers, sorbitan fatty acid esters, polyoxyethylene sorbitan fatty acid esters and the like. Adjuvants other than the above surface active agents for formulation are lignin sulfate, alginate, poly(vinyl alcohol), gum arabic, CMC (carboxymethyl cellulose), PAP (acid isopropyl phosphate) and the like.

The seed disinfectant composition of the present invention can be used for dust-coating, dipping or spraying.

In the case of dust-coating or spraying seeds with the seed disinfectant composition of the present invention, the amount of the composition used is preferably from 0.0001 to 1% as the active ingredients based on the dry weight of seeds, while in the case of dipping or spraying seeds in or with the seed disinfectant composition of the present invention, the concentration of the active ingredients in the composition is preferably from 0.01 ppm to 10%. However, the amount of the composition used is variable depending on the type of preparation or the kind of crop seed to be treated. Moreover, a wider range of seed born diseases can be prevented by applying a mixture of the seed disinfectant composition of the present invention with other disinfectants such as nuarimol, hydroxyisoxazole, basic copper chloride, imazalil and the like. Also, when anthraquinone is added thereto, the resulting disinfectant composition has a bird repellent effect, and the seed disinfectant composition of the present invention can be used in admixture with other seed-treating agents.

The seed disinfectant composition of the present invention exhibits a synergistically high preventing effect on various seed born diseases and simultaneously has a wide antifungal spectrum and shows a stable preventing effect on the fungi having resistance to conventional disinfectants. Furthermore, when seeds are treated with the seed disinfectant composition of the present invention, an improvement in germination is observed.

The seed disinfectant composition of the present invention is effective on the seed born diseases such as *Septoria tritici, Leptosphaeria nodorum, Tilletia caries, ustilago tritici, Fusarium sp., Cochliobolus sativus, Helminthosporium gramineum, Ustilago nuda, Pyrenophora teres, Rhynchosporium secalis, Ustilago hordei, Ustilago avenae, Pyrenophora avenae, Pyricularia oryzae, Cochliobolus miyabeanus, Gibberella fujikuroi* and the like.

The present invention is explained in more detail in the following examples which are by way of illustration and not by way of limitation. In the following examples, "parts" or "%" is by weight.

EXAMPLE 1

A dust containing 3.5% of the seed disinfectant composition of the present invention was obtained by thoroughly grinding and mixing the following components:

| | |
|---|---|
| Compound A | 0.5 part |
| Acetate of Compound B | 3 parts |
| Hydroxyisoxazole | 20 parts |
| Kaoline clay | 66.5 parts |
| Talc | 10 parts |

EXAMPLE 2

A wettable powder containing 5% of the seed disinfectant composition of the present invention was obtained by thoroughly grinding and mixing the following components:

| | |
|---|---|
| Compound A | 0.5 part |
| Acetate of Compound B | 4.5 parts |
| Imazalil | 5 parts |
| Diatomaceous earth | 40 parts |
| White carbon | 45 parts |
| Wetting agent (sodium lauryl sulfate) | 3 parts |
| Dispersant (calcium lignin sulfonate) | 2 parts |

EXAMPLE 3

A flowable concentrate containing 2% of the seed disinfectant composition of the present invention was obtained by mixing and wet grinding the following components so that the grain sizes of the active ingredients became not more than 5 microns:

| | |
|---|---|
| Compound A | 0.5 part |
| Sulfate of Compound B | 1.5 parts |
| Polyoxyethylene sorbitan monooleate | 3 parts |
| CMC | 3 parts |
| Water | 92 parts |

EXAMPLE 4

An emulsifiable concentrate containing 50% of the seed disinfectant composition of the present invention was obtained by mixing the following components:

| | |
|---|---|
| Compound A | 0.5 part |
| Acetate of Compound B | 49.5 parts |
| Imazalil | 1.5 parts |
| Emulsifier (polyoxyethylene alkylaryl ether) | 3.5 parts |
| Cyclohexanone | 30 parts |
| Xylene | 15 parts |

EXAMPLE 5

A wettable powder containing 50% of the seed disinfectant composition of the present invention was obtained by thoroughly grinding and mixing the following components:

| | |
|---|---|
| Compound A | 2.5 parts |
| Acetate of Compound B | 47.5 parts |
| Diatomaceous earth | 25 parts |
| White carbon | 20 parts |
| Wetting agent (sodium lauryl sulfate) | 3 parts |
| Dispersant (calcium lignin sulfonate) | 2 parts |

EXAMPLE 6

10 g of wheat seeds (variety: Norin No. 61) inoculated and infected with *Tilletia caries* were dipped into an aqueous solution containing a prescribed concentration of a wettable powder of the seed disinfectant composition of the present invention prepared in the same manner as in Example 2, for 24 hours. Thereafter, they were sown in an upland field and cultivated.

When the wheat came into ears, they were examined to determine whether they had any symptoms of the disease and the percentage of healthy seedlings was calculated from the following equation.

$$\text{Percentage of healthy seedlings} = \frac{\text{Number of healthy seedlings in treated plot}}{\text{Number of healthy seedlings in uninoculated and untreated plot}} \times 100$$

Moreover, the synergistic effect of the seed disinfectant composition of the present invention was studied according to the following procedure.

The effect (E) expected from the mixing of a compound X with another compound Y is generally given by the following equation:

$$E = m + n - \frac{m \cdot n}{100}$$

E: Preventing effect(%) (percentage of healthy seedlings) expected when a mixture of X and Y in respective amounts of p and q is used.

m: Preventing effect (%) (percentage of healthy seedlings) when X is used alone in an amount of p.

n: Preventing effect (%) (percentage of healthy seedlings) when Y is used alone in an amount of q. (See "Noyaku Jikkenho" (method of Experiment for Agricultural Chemicals), Volume: Fungicides, p. 52, published by Soft Science Mar. 31, 1981)

If the found effect obtained by mixing the two is larger than the expected one, it can be said that a synergistic effect is obtained. The results are shown in Table 1.

TABLE 1

| Sample | Content of (−)-enantiomer of Compound A (% by weight) | Active ingredient concentration for treatment (ppm) | Percentage of healthy seedlings Found | Expected |
|---|---|---|---|---|
| Compound A + | 66.5 | 1 + 9 | 96 | 57.7 |
| Acetate of | 90.2 | 1 + 9 | 98 | 68.5 |
| Compound B | 94.7 | 1 + 9 | 100 | 71.2 |
| Compound A | 66.5 | 10 | 69 | — |
|  |  | 1 | 53 | — |
|  | 90.2 | 10 | 80 | — |
|  |  | 1 | 65 | — |
|  | 94.7 | 10 | 84 | — |
|  |  | 1 | 68 | — |
| Acetate of Compound B | — | 10 | 20 | — |
|  |  | 9 | 10 | — |
| Inoculation and no treatment | — | — | 0 | — |
| No inoculation and no treatment | — | — | 100 | — |

EXAMPLE 7

Each of the flowable concentrates of the seed disinfectant composition of the present invention prepared according to Example 3 was sprayed onto 10 g of barley seeds (variety: New Golden) infected with *Helminthosporium gramineum*. Thereafter, the barley seeds were sown in an upland field and cultivated. When the barley came into ears, they were examined to determine whether they had any symptoms of the disease, the percentage of healthy seedlings was calculated in the same manner as in Example 6 and a synergistic effect was confirmed by comparing the found value with the expected value. The results are shown in Table 2.

TABLE 2

| Sample | Content of (−)-enantiomer of Compound A (% by weight) | Amount of active ingredient for treatment (g/100 kg-dry seed) | Percentage of healthy seedlings Found | Expected |
|---|---|---|---|---|
| Compound A + | 66.5 | 1 + 3 | 95 | 47.5 |
| Acetate of | 90.2 | 1 + 3 | 99 | 55.8 |
| Compound B | 94.7 | 1 + 3 | 100 | 60.3 |
| Compound A | 66.5 | 4 | 56 | — |
|  |  | 1 | 30 | — |
|  | 90.2 | 4 | 70 | — |
|  |  | 1 | 41 | — |
|  | 94.7 | 4 | 78 | — |
|  |  | 1 | 47 | — |
| Acetate of Compound B | — | 4 | 31 | — |
|  |  | 3 | 25 | — |
| Inoculation and no treatment | — | — | 0 | — |
| No inoculation and no treatment | — | — | 100 | — |

EXAMPLE 8

Grains of unhulled rice (variety: Kinki No. 33) infected with benomyl-sensitive or benomyl-resistant *Gibberella fujikuroi* were dust-coated with a prescribed amount of a dust of the seed disinfectant composition of the present invention prepared according to Example 1 or a commercially available seed disinfectant (Benlate T®). Thereafter, the unhulled rice was sown in sandy loam in a plastic pot at a rate of 100 grains per pot, covered with soil and cultivated for 16 days in a greenhouse. Then, the symptoms of the disease was examined and the percentage of healthy seedlings was calculated in the same manner as in Example 6. The results are shown in Table 3.

TABLE 3

| Sample | Content of (−)-enantiomer of Compound A (% by weight) | Amount of active ingredient for treatment (g/100 kg-dry seed) | Percentage of healthy seedlings a[*2] | b[*3] |
|---|---|---|---|---|
| Compound A + Acetate of Compound B | 90.2 | 2 + 5 | 100 | 100 |
|  |  | 1 + 2.5 | 100 | 100 |
| Benlate T[*1] | — | 50 + 50 | 100 | 78 |
|  |  | 25 + 25 | 93 | 56 |
| Inoculation and no treatment | — | — | 31 | 24 |
| No inoculation and no treatment | — | — | 100 | 100 |

EXAMPLE 9

An emulsifiable concentrate of the seed disinfectant composition of the present invention prepared according to Example 4 was sprayed onto 10 g of barley seeds (variety: Video) infected with *Ustilago nuda*. Thereafter, the barley seeds were sown in an upland field and cultivated. When the barley came into ears, they were examined to determine whether they had any symptoms of the disease, the percentage of healthy seedlings was calculated in the same manner as in Example 6 and a synergistic effect was confirmed by comparing the found value with the expected value. The results are shown in Table 4.

TABLE 4

| Sample | Content of (−)-enantiomer of Compound A (% by weight) | Amount of active ingredient for treatment (g/100 kg-dry seed) | Percentage of healthy seedlings Found | Expected |
|---|---|---|---|---|
| Compound A + Acetate of Compound B | 66.5 | 1 + 8 | 97 | 75.2 |
|  |  | 0.5 + 20 | 95 | 64.8 |
|  | 90.2 | 1 + 8 | 99 | 79.8 |

TABLE 4-continued

| Sample | Content of (−)-enantiomer of Compound A (% by weight) | Amount of active ingredient for treatment (g/100 kg-dry seed) | Percentage of healthy seedlings Found | Percentage of healthy seedlings Expected |
|---|---|---|---|---|
| | | 0.5 + 20 | 96 | 71.8 |
| | 94.7 | 1 + 8 | 100 | 82.5 |
| | | 0.5 + 20 | 96 | 75.4 |
| Compound A | 66.5 | 20.5 | 100 | — |
| | | 9 | 100 | — |
| | | 1 | 73 | — |
| | | 0.5 | 60 | — |
| | 90.2 | 20.5 | 100 | — |
| | | 9 | 100 | — |
| | | 1 | 78 | — |
| | | 0.5 | 68 | — |
| | 94.7 | 20.5 | 100 | — |
| | | 9 | 100 | — |
| | | 1 | 81 | — |
| | | 0.5 | 72 | — |
| Acetate of Compound B | — | 20.5 | 13 | — |
| | | 20 | 12 | — |
| | | 9 | 11 | — |
| | | 8 | 8 | — |
| Inoculation and no treatment | — | — | 0 | — |
| No inoculation and no treatment | — | — | 100 | — |

EXAMPLE 10

A flowable concentrate of the seed disinfectant composition of the present invention prepared according to Example 3 was sprayed onto 10 g of barley seeds (variety: Panda) or wheat seeds (variety: Avalon). Thereafter, the seeds were sown in sady loam in plastic pots and cultimated in a greenhouse while keeping the temperature at 20° C. Seven days later, their germinations were examined. The results are shown in Table 5.

TABLE 5

| Sample | Content of (−)-enantiomer of Compound A (% by weight) | Amount of active ingredient for treatment (g/100 kg-dry seed) | Germination (%) barley | Germination (%) wheat |
|---|---|---|---|---|
| Compound A + Acetate of Compound B | 66.5 | 4 + 8 | 98 | 90 |
| | 90.2 | 4 + 8 | 99 | 93 |
| | 94.7 | 4 + 8 | 99 | 95 |
| Compound A | 66.5 | 12 | 83 | 64 |
| | | 4 | 82 | 61 |
| | 90.2 | 12 | 85 | 66 |
| | | 4 | 83 | 63 |
| | 94.7 | 12 | 86 | 69 |
| | | 4 | 83 | 65 |
| Acetate of Compound B | — | 12 | 83 | 65 |
| | | 8 | 81 | 61 |
| No treatment | — | — | 81 | 61 |

It was observed that the germination was improved by using a mixture of Compound A and an acetate of Compound B.

What is claimed is:

1. A method for preventing or treating fungal infections of seeds which comprises applying to the seeds a fungicidally effective amount of a seed disinfectant composition comprising (A) (E)-1-(2,4-dichlorophenyl)-4,4-dimethyl-2-(1, 2,4-triazol-1-yl)-1-penten-3-ol containing not less than 50% by weight of (-)-(E)-1-(2,4-dichlorophenyl)-4,4-dimethyl-2-(1,2,4,-triazol-1-yl)-1-penten-3-ol and (B) the acetate salt of 1,1'-iminodi(octamethylene)-diguanidine as active ingredients, the weight ratio of (A)×(B) ranging from 1:2 to 1:40.

* * * * *